United States Patent
Otsuka

(10) Patent No.: US 12,287,277 B2
(45) Date of Patent: Apr. 29, 2025

(54) INFORMATION PROCESSING APPARATUS, PARTICLE MEASURING APPARATUS, PARTICLE MEASURING SYSTEM, PARTICLE DISPENSING APPARATUS, PARTICLE DISPENSING SYSTEM, INFORMATION PROCESSING METHOD, AND INFORMATION PROCESSING PROGRAM

(71) Applicant: Sony Group Corporation, Tokyo (JP)

(72) Inventor: Fumitaka Otsuka, Kanagawa (JP)

(73) Assignee: Sony Group Corporation, Tokyo (JP)

( * ) Notice: Subject to any disclaimer, the term of this patent is extended or adjusted under 35 U.S.C. 154(b) by 378 days.

(21) Appl. No.: 17/787,056

(22) PCT Filed: Nov. 18, 2020

(86) PCT No.: PCT/JP2020/042950
§ 371 (c)(1),
(2) Date: Jun. 17, 2022

(87) PCT Pub. No.: WO2021/131415
PCT Pub. Date: Jul. 1, 2021

(65) Prior Publication Data
US 2023/0031689 A1   Feb. 2, 2023

(30) Foreign Application Priority Data

Dec. 25, 2019 (JP) .................. 2019-235031

(51) Int. Cl.
*G01N 15/14* (2024.01)
*G01N 15/1434* (2024.01)

(52) U.S. Cl.
CPC . *G01N 15/1434* (2013.01); *G01N 2015/1402* (2013.01); *G01N 2015/1477* (2013.01)

(58) Field of Classification Search
CPC ........... G01N 15/1459; G01N 15/1434; G01N 15/1429; G01N 15/01; G01N 2015/1006;
(Continued)

(56) References Cited

U.S. PATENT DOCUMENTS

2006/0015291 A1   1/2006 Parks et al.
2013/0229412 A1*  9/2013 Suzuki ................ H04N 13/275
                                                          345/419
(Continued)

FOREIGN PATENT DOCUMENTS

JP   2007-132921 A   5/2007
JP   2019-174543 A   10/2019

OTHER PUBLICATIONS

International Search Report and English translation thereof mailed Jan. 26, 2021 in connection with International Application No. PCT/JP2020/042950.
(Continued)

*Primary Examiner* — Sang H Nguyen
(74) *Attorney, Agent, or Firm* — Wolf, Greenfield & Sacks, P.C.

(57) ABSTRACT

The present technology is to provide technology for appropriately visualizing a population of particles in particle analysis technology.

There is provided an information processing apparatus including an information processing unit that receives optical data obtained from particles, and calculates a parameter that specifies a display method of the optical data in a display range having at least one axis including a linear axis and a logarithmic axis on the basis of the received optical data, in which the parameter includes a first parameter that specifies a range of the linear axis and a second parameter that specifies a lower limit value of the display range, and the
(Continued)

first parameter and the second parameter are calculated on the basis of different reference values.

17 Claims, 5 Drawing Sheets

(58) Field of Classification Search
CPC ......... G01N 15/149; G01N 2015/1477; G01N 2015/1402; G16B 40/10
See application file for complete search history.

(56) References Cited

U.S. PATENT DOCUMENTS

2014/0222381 A1* 8/2014 Nitta ..................... G01J 3/0264
702/189
2014/0240314 A1* 8/2014 Fukazawa ............... G06T 15/00
345/419
2014/0294281 A1* 10/2014 Suzuki .................... G06T 19/00
382/133
2017/0074863 A1* 3/2017 Masuda ................... G01N 1/38
2018/0348112 A1* 12/2018 Nagai .................. G01N 1/4077

OTHER PUBLICATIONS

Moore et al., Update for the Logicle Data Scale Including Operational Code Implementations. Communication to the Editor. Cytometry Part A. 2012(81A):273-77.

Parks et al., A New "Logicle" Display Method Avoids Deceptive Effects of Logarithmic Scaling for Low Signals and Compensated Data. Cytometry Part A. 2006(69A):541-51.

* cited by examiner

BEFORE PARAMETER APPLICATION     AFTER PARAMETER APPLICATION

INFORMATION PROCESSING APPARATUS, PARTICLE MEASURING APPARATUS, PARTICLE MEASURING SYSTEM, PARTICLE DISPENSING APPARATUS, PARTICLE DISPENSING SYSTEM, INFORMATION PROCESSING METHOD, AND INFORMATION PROCESSING PROGRAM

CROSS-REFERENCE TO RELATED APPLICATIONS

This application claims the benefit under 35 U.S.C. § 371 as a U.S. National Stage Entry of International Application No. PCT/JP2020/042950, filed in the Japanese Patent Office as a Receiving Office on Nov. 18, 2020, which claims priority to Japanese Patent Application Number JP2019-235031, filed in the Japanese Patent Office on Dec. 25, 2019, each of which is hereby incorporated by reference in its entirety.

TECHNICAL FIELD

The present technology relates to an information processing apparatus. More specifically, the present technology relates to an information processing apparatus, a particle measuring apparatus, a particle measuring system, a particle dispensing apparatus, a particle dispensing system, an information processing method, and an information processing program that are used for optically measuring characteristics of particles.

BACKGROUND ART

In recent years, with the development of analytical techniques, techniques for individually measuring particles and the like and analyzing or dispensing the measured particles and the like in a process of causing biological microparticles such as cells and microorganisms, microparticles such as microbeads, and the like to flow through a flow path have been developed.

As one representative example of such techniques for analyzing or dispensing particles, technical improvement of an analysis technique called flow cytometry has been rapidly progressing. The flow cytometry is an analysis technique in which analysis target particles are caused to flow in a state aligned in a fluid, and the particles are irradiated with laser light or the like to detect fluorescence or scattered light emitted from each of the particles, thereby analyzing or dispensing the particles.

For example, in a case where fluorescence of a cell is detected, a cell labeled with a fluorescent dye is irradiated with excitation light having an appropriate wavelength and intensity, such as laser light. Then, the fluorescence emitted from the fluorescent dye is condensed by a lens or the like, light in an appropriate wavelength region is selected using a wavelength selection element such as a filter or a dichroic mirror, and the selected light is detected using a light receiving element such as a photo multiplier tube (PMT). At this time, by combining a plurality of wavelength selection elements and light receiving elements, it is also possible to simultaneously detect and analyze fluorescence from a plurality of fluorescent dyes labeled on the cell. Moreover, a number of analyzable fluorescent dyes can be increased by combining excitation lights of a plurality of wavelengths.

For fluorescence detection in the flow cytometry, there is also a method of measuring an intensity of light in a continuous wavelength region as a fluorescence spectrum, in addition to a method of selecting a plurality of lights in a discontinuous wavelength regions using a wavelength selection element such as a filter and measuring an intensity of light in each of the wavelength regions. In spectral flow cytometry capable of measuring a fluorescence spectrum, fluorescence emitted from particles is dispersed using a spectroscopic element such as a prism or a grating. Then, the dispersed fluorescence is detected using a light receiving element array in which a plurality of light receiving elements having different detection wavelength regions is arranged. As the light receiving element array, a PMT array or a photodiode array in which light receiving elements such as PMTs or photodiodes are one-dimensionally arranged is used. Alternatively, a light receiving element array in which a plurality of independent detection channels such as two-dimensional light receiving elements including CODs or CMOSs is arranged is used.

In the analysis of particles represented by the flow cytometry or the like, an optical method of irradiating analysis target particles with light such as laser and detecting fluorescence or scattered light emitted from the particles is often used. Then, a histogram is extracted by a computer and software for analysis on the basis of detected optical information, and the analysis is performed.

For example, Patent Document 1 proposes a method for identifying a population of events in multidimensional data such as seven-dimensional flow cytometry data of a blood sample, for example, data representing different white blood cell components or the like in the sample.

CITATION LIST

Patent Document

Patent Document 1: Japanese Patent Application Laid-Open No. 2007-132921

Non-Patent Documents

Non-Patent Document 1: Cytometry Part A 69A: 541-551, 2006
Non-Patent Document 2: Cytometry Part A 81A: 273-277, 2012

SUMMARY OF THE INVENTION

Problems to be Solved by the Invention

In the particle analysis technique such as the flow cytometer, for example, the methods described in Non-Patent Documents 1 and 2 are widely used. However, in the methods described in Non-Patent Documents 1 and 2, in order to appropriately display the population of particles, it is necessary to appropriately adjust various parameters, and there is a problem that time-consuming work involving complicated manual operation is required.

Furthermore, in the methods described in Non-Patent Documents 1 and 2, a numerical value for specifying a lower limit value of a display area is fixed, and there is also a problem that a certain proportion of data having a small value in all data is not displayed, and there is also a problem that a case where data is not appropriately displayed for various populations occurs.

Therefore, a main object of the present technology is to provide a technology for appropriately visualizing a population of particles in particle analysis technology.

Solutions to Problems

The present technology first provides an information processing apparatus including:
an information processing unit that receives optical data obtained from particles, and
calculates a parameter that specifies a display method of the optical data in a display range having at least one axis including a linear axis and a logarithmic axis on the basis of the received optical data,
in which the parameter includes a first parameter that specifies a range of the linear axis and a second parameter that specifies a lower limit value of the display range, and
the first parameter and the second parameter are calculated on the basis of different reference values.

In the information processing apparatus according to the present technology, the display range may have at least two axes including the linear axis and the logarithmic axis, and
the information processing unit may calculate the parameter for each of at least the two axes.

In the information processing apparatus according to the present technology, the parameter may further include a third parameter that specifies an upper limit value of the display range.

In the information processing apparatus according to the present technology, the information processing unit may calculate the first parameter by the following formula (1).

$$W = \text{Log}(\text{abs}(r)/(d))$$

$$(r = (n)\text{percentile} \times (m)) \quad (1)$$

In the information processing apparatus according to the present technology, the information processing unit may calculate the second parameter by a following formula (2).

$$\text{Min} = (c)\text{percentile} \quad (2)$$

The information processing apparatus according to the present technology, the parameter may further include a third parameter that specifies an upper limit value of the display range, and the information processing apparatus may calculate the third parameter by a following formula (3).

$$\text{Max} = (a)\text{percentile} \times (b) \quad (3)$$

In the information processing apparatus according to the present technology, the parameter further may include a fourth parameter that specifies a range of the linear axis of data of a negative area in the optical data, and the information processing unit may calculate the fourth parameter by a following formula (4).

$$A = \text{Log}(\text{Min}/r)$$

$$(r = (n)\text{percentile} \times (m)) \quad (4)$$

In the information processing apparatus according to the present technology, the information processing unit may calculate the parameter on the basis of an instruction of a user.

The information processing apparatus according to the present technology may further include a storage unit that stores the optical data, in which the information processing unit may calculate the parameter on the basis of optical data received from the storage unit on the basis of an instruction of the user.

In the information processing apparatus according to the present technology, the information processing unit may create a graph illustrating the optical data on the display range using the display method specified on the basis of the parameter.

The information processing apparatus according to the present technology may further include a storage unit that stores the graph.

Next, the present technology provides a particle measuring apparatus including:
a light detection unit that detects optical data from particles flowing in a flow path; and
an information processing unit that receives the detected optical data, and
calculates a parameter that specifies a display method of the optical data in a display range having at least one axis including a linear axis and a logarithmic axis on the basis of the received optical data,
in which the parameter includes a first parameter that specifies a range of the linear axis and a second parameter that specifies a lower limit value of the display range, and
the first parameter and the second parameter are calculated on a basis of different reference values.

The present technology also provides a particle measuring system including:
a light detecting apparatus that detects optical data from particles flowing in a flow path; and
an information processing apparatus having an information processing unit that receives the detected optical data, and
calculates a parameter that specifies a display method of the optical data in a display range having at least one axis including a linear axis and a logarithmic axis on the basis of the received optical data,
in which the parameter includes a first parameter that specifies a range of the linear axis and a second parameter that specifies a lower limit value of the display range, and
the first parameter and the second parameter are calculated on the basis of different reference values.

The present technology further provides a particle dispensing apparatus including:
a light detection unit that detects optical data from particles flowing in a flow path;
an information processing unit that receives the detected optical data, and
calculates a parameter that specifies a display method of the optical data in a display range having at least one axis including a linear axis and a logarithmic axis on the basis of the received optical data,
in which the parameter includes a first parameter that specifies a range of the linear axis and a second parameter that specifies a lower limit value of the display range, and
the first parameter and the second parameter are calculated on the basis of different reference values; and
a dispensing unit that dispenses the particles on the basis of the detected optical data.

The present technology also provides a particle dispensing system including:
a light detecting apparatus that detects optical data from particles flowing in a flow path;
an information processing apparatus having an information processing unit that receives the detected optical data, and
calculates a parameter that specifies a display method of the optical data in a display range having at least one axis including a linear axis and a logarithmic axis on the basis of the received optical data, in which the parameter includes a first parameter that specifies a range of the linear axis and a second parameter that specifies a lower limit value of the display range, and the first parameter and the second parameter are calculated on the basis of different reference values; and a dispensing apparatus that dispenses the particles on the basis of the detected optical data.

The present technology provides an information processing method including an information processing step of receiving optical data obtained from particles, and calculating a parameter that specifies a display method of the optical data in a display range having at least one axis including a linear axis and a logarithmic axis on the basis of the received optical data, in which the parameter includes a first parameter that specifies a range of the linear axis and a second parameter that specifies a lower limit value of the display range, and the first parameter and the second parameter are calculated on the basis of different reference values.

The present technology provides an information processing program that causes a computer to implement an information processing function of receiving optical data obtained from particles, calculating a parameter that specifies a display method of the optical data in a display range having at least one axis including a linear axis and a logarithmic axis on the basis of the received optical data, in which the parameter includes a first parameter that specifies a range of the linear axis and a second parameter that specifies a lower limit value of the display range, and the first parameter and the second parameter are calculated on the basis of different reference values.

In the present technology, the "particles" widely include bio-related microparticles such as cells, microorganisms, and liposomes, synthetic particles such as latex particles, gel particles, and industrial particles, and the like.

The bio-related microparticles include chromosomes, liposomes, mitochondria, organelles, and the like constituting various cells. The cells include animal cells (for example, blood cells and the like) and plant cells. The microorganisms include bacteria such as *Escherichia coli*, viruses such as tobacco mosaic virus, fungi such as yeast, and the like. Moreover, the bio-related microparticles may also include bio-related polymers such as nucleic acids, proteins, and complexes thereof. Furthermore, the industrial particles may be, for example, organic or inorganic polymer materials, metals, or the like. The organic polymer materials include polystyrene, styrene-divinylbenzene, polymethyl methacrylate, and the like. The inorganic polymer materials include glass, silica, and magnetic materials and the like. The metals include gold colloid, aluminum, and the like. A shape of each of these particles is generally spherical, but may be non-spherical in the present technology, and in addition, a size, a mass, and the like thereof are not particularly limited.

MODE FOR CARRYING OUT THE INVENTION

Figure 1:
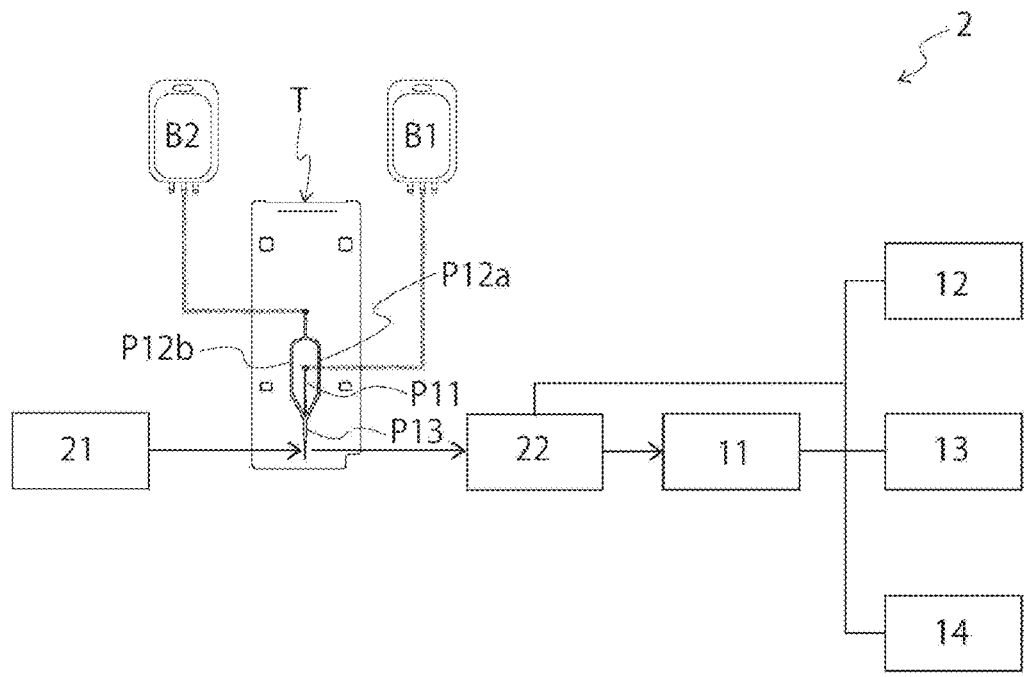
FIG. 1 is a schematic conceptual diagram schematically illustrating one example of an embodiment of a particle measuring apparatus 2 that can use an information processing apparatus 1 according to the present technology.

Hereinafter, embodiments for carrying out the present technology will be described. The embodiments described below describe examples of representative embodiments of the present technology, and the scope of the present technology is not narrowly interpreted by this. Note that description will be given in the following order.

1. Information Processing Apparatus 1, Particle Measuring Apparatus 2, Particle Measuring System 20, Particle Dispensing Apparatus 3, Particle Dispensing System 30
   (1) Flow path P
   (2) Light irradiation unit 21
   (3) Light detection unit 22
   (4) Information processing apparatus 1
   (4-1) Information processing unit 11
   (4-2) Storage unit 12
   (4-3) Display unit 13
   (4-4) User interface 14
   (5) Dispensing unit 31
2. Information Processing Method, Particle Measuring Method, and Particle Dispensing Method
3. Information Processing Program <1. Information Processing Apparatus 1, Particle Measuring Apparatus 2, Particle Measuring System 20, Particle Dispensing Apparatus 3, Particle Dispensing System 30>

Figure 2:
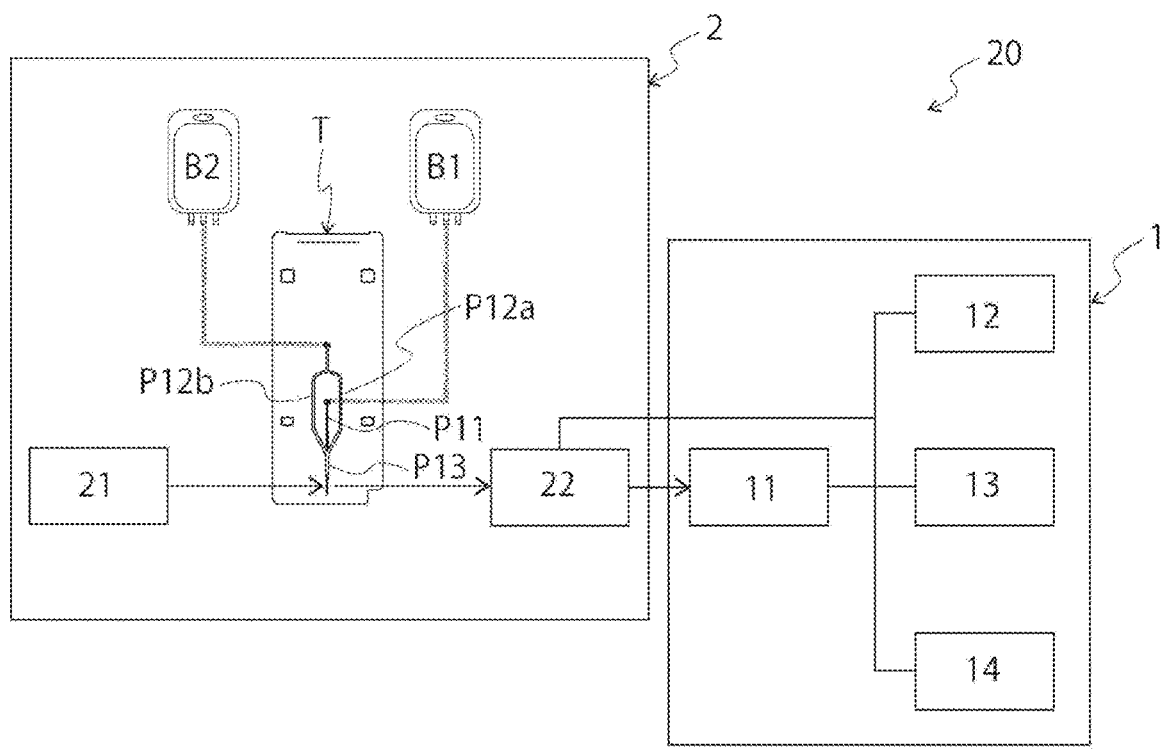
FIG. 2 is a schematic conceptual diagram schematically illustrating one example of an embodiment of a particle measuring system 20 that can use the information processing apparatus 1 according to the present technology.
Figure 3:
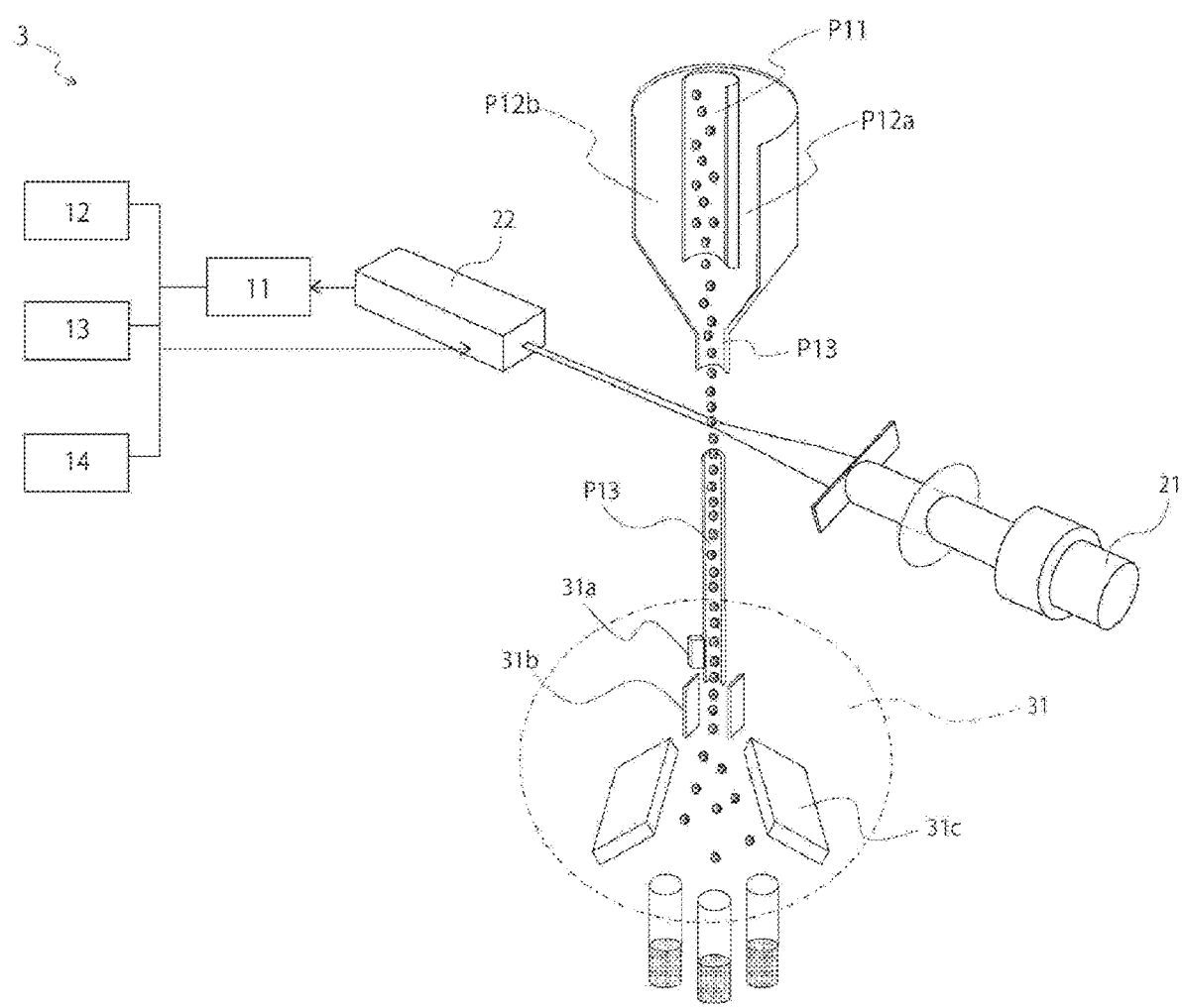
FIG. 3 is a schematic conceptual diagram schematically illustrating one example of an embodiment of a particle dispensing apparatus 3 that can use the information processing apparatus 1 according to the present technology.
Figure 4:
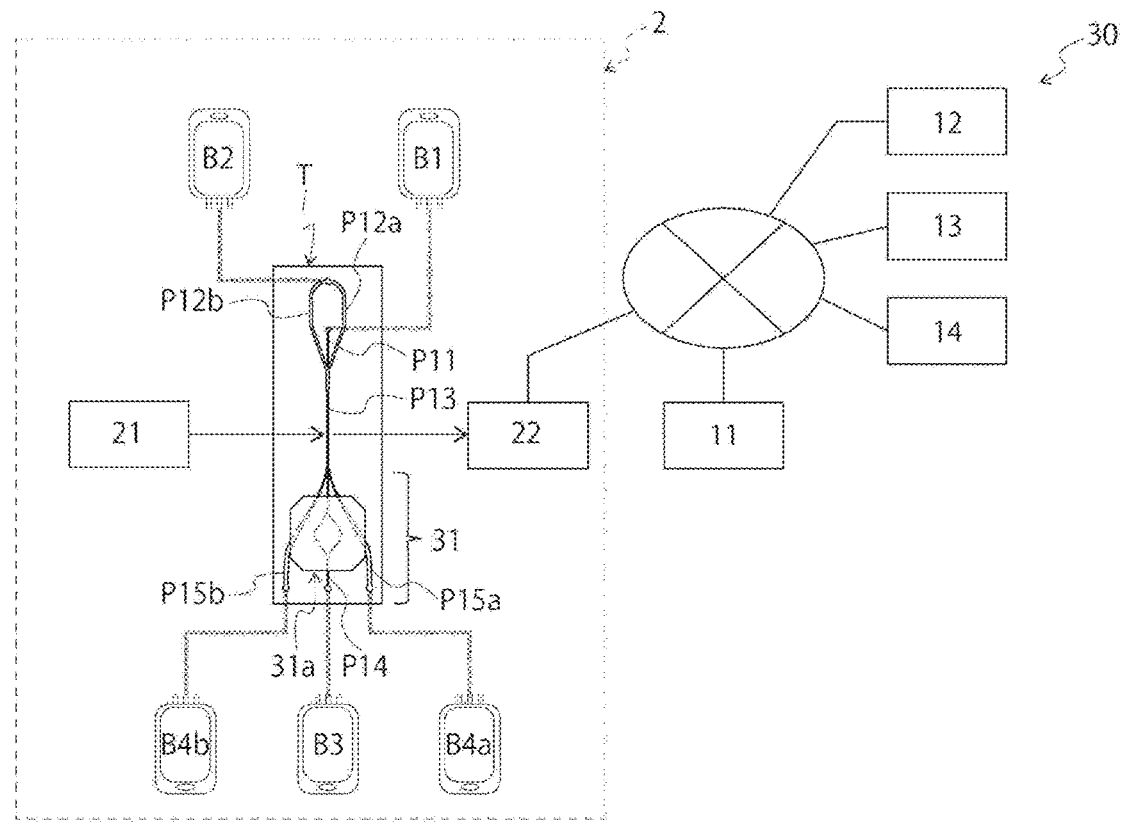
FIG. 4 is a schematic conceptual diagram schematically illustrating one example of an embodiment of a particle dispensing system 30 that can use the information processing apparatus 1 according to the present technology.

FIG. 1 is a schematic conceptual diagram schematically illustrating one example of an embodiment of a particle measuring apparatus 2 that can use an information processing apparatus 1 according to the present technology. FIG. 2 is a schematic conceptual diagram schematically illustrating one example of an embodiment of a particle measuring system 20 that can use the information processing apparatus 1 according to the present technology. FIG. 3 is a schematic conceptual diagram schematically illustrating one example of an embodiment of a particle dispensing apparatus 3 that can use the information processing apparatus 1 according to the present technology. FIG. 4 is a schematic conceptual diagram schematically illustrating one example of an embodiment of a particle dispensing system 30 that can use the information processing apparatus 1 according to the present technology. The particle measuring apparatus 2 and the particle measuring system 3 according to the present technology include at least a light detection unit 22 and an information processing unit 11 (information processing apparatus 1). The particle dispensing apparatus 3 and the particle dispensing system 30 according to the present technology include at least the light detection unit 22, the information processing unit 11 (the information processing apparatus 1), and a dispensing unit 31. Furthermore, a flow path P, a light irradiation unit 21, a storage unit 12, a display unit 13, a user interface 14, and the like can be included as necessary.

Note that the information processing unit 11, the storage unit 12, the display unit 13, the user interface 14, and the like may be independently provided like the particle measuring apparatus 2 shown in FIG. 1 or the particle dispensing apparatus 3 shown in FIG. 3, or as shown in FIG. 2, the particle measuring system 20 configured of the information processing apparatus 1 including the information processing unit 11, the storage unit 12, the display unit 13, and the user interface 14, and the particle measuring apparatus 2 may be provided. Moreover, as shown in FIG. 4, the information processing unit 11, the storage unit 12, the display unit 13, and the user interface 14 that are independent from each other can be connected to the light detection unit 22 of the particle dispensing apparatus 3 via a network to configure the particle dispensing system 30.

Moreover, the information processing unit 11 and the storage unit 12 can be provided in a cloud environment and connected to the particle measuring apparatus 2 and the particle dispensing apparatus 3 via a network. More preferably, the information processing unit 11 and the display unit 13 can be provided in the information processing apparatus 1, and the storage unit 12 can be provided in a cloud environment and connected to the particle measuring apparatus 2 and the particle dispensing apparatus 3 via a network. In this case, a record or the like of information processing in the information processing unit 11 can be stored in the storage unit 12 on a cloud, and various types of information stored in the storage unit 12 can be shared by a plurality of users.

Hereinafter, details of each of the units will be described along time series of measurement.

(1) Flow Path P

The particle measuring apparatus 2, the particle measuring system 20, the particle dispensing apparatus 3, and the particle dispensing system 30 according to the present technology can analyze and dispense particles by detecting optical information obtained from particles aligned in a line in a flow cell (flow path P).

While the flow path P may be included in advance in the particle measuring apparatus 2, the particle measuring system 20, the particle dispensing apparatus 3, and the particle dispensing system 30, it is also possible to perform analysis or dispensing by installing a commercially available flow path P, a disposable chip provided with the flow path P, or the like.

A form of the flow path P is also not particularly limited, and can be freely designed. For example, not only the flow path P formed in a substrate T of two-dimensional or three-dimensional plastic or glass as shown in FIGS. 1, 2, and 4, but also a flow path P used in a conventional flow cytometer as shown in FIG. 3 can be used for the particle measuring apparatus 2.

Furthermore, a flow path width, a flow path depth, and a flow path cross-sectional shape of the flow path P are not particularly limited as long as they can form a laminar flow, and can be freely designed. For example, a micro flow path having a flow path width of 1 mm or less can also be used for the particle measuring apparatus 2. In particular, a micro flow path having a flow path width of about 10 μm or more and 1 mm or less can be suitably used in the present technology.

A method for feeding the particles is not particularly limited, and the particles can be caused to flow in the flow path P according to the form of the flow path P to be used. For example, a case of the flow path P formed in the substrate T each shown in FIGS. 1, 2, and 4 will be described. A sample liquid containing the particles is introduced into a sample liquid flow path P11, and a sheath liquid is introduced into two sheath liquid flow paths P12a and P12b, respectively. The sample liquid flow path P11 and the sheath liquid flow paths P12a, P12b merge into a main flow path P13. A sample liquid laminar flow fed in the sample liquid flow path P11 and a sheath liquid laminar flow fed in the sheath liquid flow paths P12a, P12b merge in the main flow path P13, and a sheath flow in which the sample liquid laminar flow is sandwiched between the sheath liquid laminar flows can be formed.

The particles flowing through the flow path P can be labeled with one or more dyes such as fluorescent dyes. In this case, as the fluorescent dyes that can be used in the present technology, for example, cascade blue, pacific blue, fluorescein isothiocyanate (FITC), phycoerythrin (PE), propidium iodide (PI), texas red (TR), peridinin chlorophyll protein (PerCP), allophycocyanin (APC), 4',6-diamidino-2 phenylindole (DAPI), Cy3, Cy5, Cy7, and brilliant violet (BV421), and the like can be cited.

(2) Light Irradiation Unit 21

The particle measuring apparatus 2, the particle measuring system 20, the particle dispensing apparatus 3, and the particle dispensing system 30 according to the present technology can each include the light irradiation unit 21. The light irradiation unit 21 irradiates the particles flowing through the flow path P with light. In the particle measuring apparatus 2, the particle measuring system 20, the particle dispensing apparatus 3, and the particle dispensing system 30 according to the present technology, the light irradiation unit 21 is not essential, and it is also possible to irradiate the particles flowing through the flow path P with light using an external light irradiation apparatus or the like.

The light irradiation unit 21 may include a plurality of light sources so that excitation light having different wavelengths can be emitted.

A type of light emitted from the light irradiation unit 21 is not particularly limited, but light having a constant light direction, wavelength, and light intensity is desirable in order to reliably generate fluorescence and scattered light from the particles. Examples thereof include a laser, an LED, and the like. In the case of using a laser, a type thereof is not particularly limited, and one or more of an argon ion (Ar) laser, a helium-neon (He—Ne) laser, a dye laser, a krypton (Cr) laser, a semiconductor laser, a solid-state laser combining a semiconductor laser and a wavelength conversion optical element, and the like can be freely used in combination.

(3) Light Detection Unit 22

The light detection unit 22 optically detects the particles flowing in the flow path P. Specifically, fluorescence or scattered light emitted from the particles is detected and converted into an electric signal. Then, the electric signal is output to the information processing unit 11 described later.

In the present technology, a specific light detection method that can be used for the light detection unit 22 is not particularly limited as long as a light detector can detect the light signal from the particles, and a light detection method used for a known light detector can be freely selected and adopted. For example, one or more types of light detection methods can be freely combined and adopted, the light detection methods being each used for a fluorescence measuring instrument, a scattered-light measuring instrument, a transmitted light measuring instrument, a reflected-light measuring instrument, a diffracted-light measuring instrument, an ultraviolet spectrometer, an infrared spectrometer, a Raman spectrometer, a FRET measuring instrument, a FISH measuring instrument, and other various spectrum measuring instruments, a PMT array or a photodiode array in which light receiving elements such as PMTs and photodiodes are one-dimensionally arranged, or a light detector in which a plurality of independent detection channels such as two-dimensional light receiving elements including CODs or CMOSs is arranged, or the like.

(4) Information Processing Apparatus 1

The information processing apparatus 1 according to the present technology is an apparatus that receives optical data obtained from the particles and processes the received optical data, and includes at least the information processing unit 11. Furthermore, the storage unit 12, the display unit 13, the user interface 14, and the like can be included as necessary.

(4-1) Information Processing Unit 11

The information processing unit 11 calculates a parameter that specifies a display method of the optical data in a display range having at least one axis including a linear axis and a logarithmic axis on the basis of the received optical data. The display range at this time has at least two axes each including the linear axis and the logarithmic axis, and the parameter can also be calculated for each of at least the two axes.

In the present technology, the parameter includes a first parameter that specifies a range of the linear axis and a second parameter that specifies a lower limit value of the display range. Then, the first parameter and the second parameter are calculated on the basis of different reference values. In the present technology, in this manner, by calculating the first parameter that specifies the range of the linear axis and the second parameter that specifies the lower limit value of the display range on the basis of different reference values, it is possible to appropriately visualize various populations of the particles.

Furthermore, in addition to the first parameter and the second parameter, the information processing unit 11 can also calculate a third parameter that specifies an upper limit value of the display range and a fourth parameter that specifies a range of the linear axis of data of a negative area in the optical data. Hereinafter, a specific calculation method of each of the parameters will be described.

(a) First Parameter

The first parameter is a parameter that specifies the range of the linear axis. This first parameter can be calculated by, for example, the following formula (1).

$$W = \text{Log}(\text{abs}(r)/(d)) \quad (1)$$

$$(r=(n)\text{percentile}\times(m))$$

In the above formula (1), specific numerical values of n, m, d can be appropriately set in accordance with a purpose. For example, it is possible to set numerical values such as n=1 to 3, m=1 to 5, and d=10 to 20, or the like.

(b) Second Parameter

The second parameter is a parameter that specifies the lower limit value of the display range. This second parameter can be calculated by, for example, the following formula (2).

$$\text{Min} = (c)\text{percentile} \quad (2)$$

In the above formula (2), specific numerical values of c can be appropriately set in accordance with a purpose. For example, it is possible to set numerical values such as c=0.3 to 1 or the like.

(c) Third Parameter

The third parameter is a parameter that specifies the upper limit value of the display range. In the conventional particle analysis technology, since the upper limit value of the display range is fixed, there is a problem that display is not appropriately performed for various populations. However, in the present technology, by using this third parameter, the upper limit value of the display range can be appropriately displayed in accordance with various populations. This third parameter can be calculated by, for example, the following formula (3).

$$\text{Max} = (a)\text{percentile} \times (b) \quad (3)$$

In the above formula (3), specific numerical values of a, b can be appropriately set in accordance with a purpose. For example, it is possible to set numerical values such as a=98 to 99.5, b=3 to 5, or the like.

Note that if a calculation result of the third parameter is not included in the specific numerical range, processing of adjusting the value so that the value is within the range may be added. As the specific numerical range, for example, a value of 1000 or more and 1 million or less can be set.

(d) Fourth Parameter

The fourth parameter is a parameter that specifies the range of the linear axis of the data of the negative area of the optical data. This fourth parameter can be calculated by, for example, the following formula (4).

$$A = \text{Log}(\text{Min}/r)$$

$$(r=(n)\text{percentile}\times(m)) \quad (4)$$

In the above formula (4), specific numerical values of n, m can be appropriately set in accordance with a purpose. For example, it is possible to set numerical values such as n=1 to 3, m=1 to 5, or the like.

(e) Fifth Parameter

A fifth parameter is a parameter that defines display of the entire optical data. This fifth parameter can be calculated by, for example, the following formula (5).

$$M = \text{Log}(\text{Max}) \quad (5)$$

Furthermore, when the fourth parameter is set, the fifth parameter can be calculated by, for example, the following formula (6).

$$M = \text{Log}(\text{Max}) + A \quad (6)$$

Scaling can be performed by substituting the parameters calculated as described above into, for example, a conversion formula such as the following formula (7).

[Expression 1]

$$S(X; T, W, M) = T \cdot 10^{-(M-W)} \cdot \left(10^{X-W} - p^2 \cdot 10^{-(X-W)/p} + p^2 - 1\right), \quad (7)$$

for $X \geq W$ $$W = 2p \cdot \frac{\log(p)}{p+1}$$

W: the parameter that specifies the range of the linear axis
M: the parameter that defines the entire display range
T: the upper limit value of the display area (the third parameter (Max))
X: coordinates of the display area
S: an input value Furthermore, when the fourth parameter is set, scaling can be performed by substituting the parameters into a conversion formula such as the following formula (8).

[Expression 2]

$$S(X; T, W, M, A) = \qquad (8)$$
$$T \cdot 10^{-(M-W-A)} \cdot \left(10^{X-W-A} - p^2 \cdot 10^{-(X-W-A)/p} + p^2 - 1\right),$$
$$\text{for } X \geq W + A$$
$$W = 2p \cdot \frac{\log(p)}{p+1}$$

Figure 5:
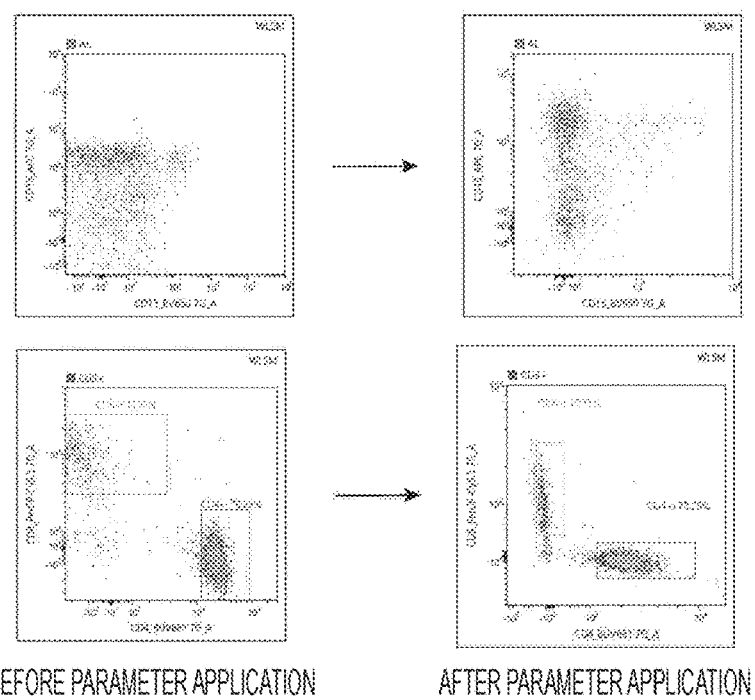
FIG. 5 is drawing-substituting graphs each illustrating one example of a graph illustrating optical data on a display range specified on the basis of parameters calculated by an information processing unit 11.

W: the parameter that specifies the range of the linear axis
M: the parameter that defines the entire display range
T: the upper limit value of the display area (the third parameter (Max))
X: the coordinates of the display area
S: the input value The information processing unit 11 can create a graph illustrating the optical data on the display range specified on the basis of the parameters calculated in this manner. FIG. 5 shows examples of graphs each illustrating the optical data on the display range specified on the basis of the parameters calculated by the information processing unit 11.

As shown in FIG. 5, while in each of the graphs before the application of the parameters, it is difficult to distinguish between the data (positive data) in a positive area and the data (negative data) of the negative area, in each of the graphs after the application of the parameters, it can be clearly distinguished.

Figure 6:
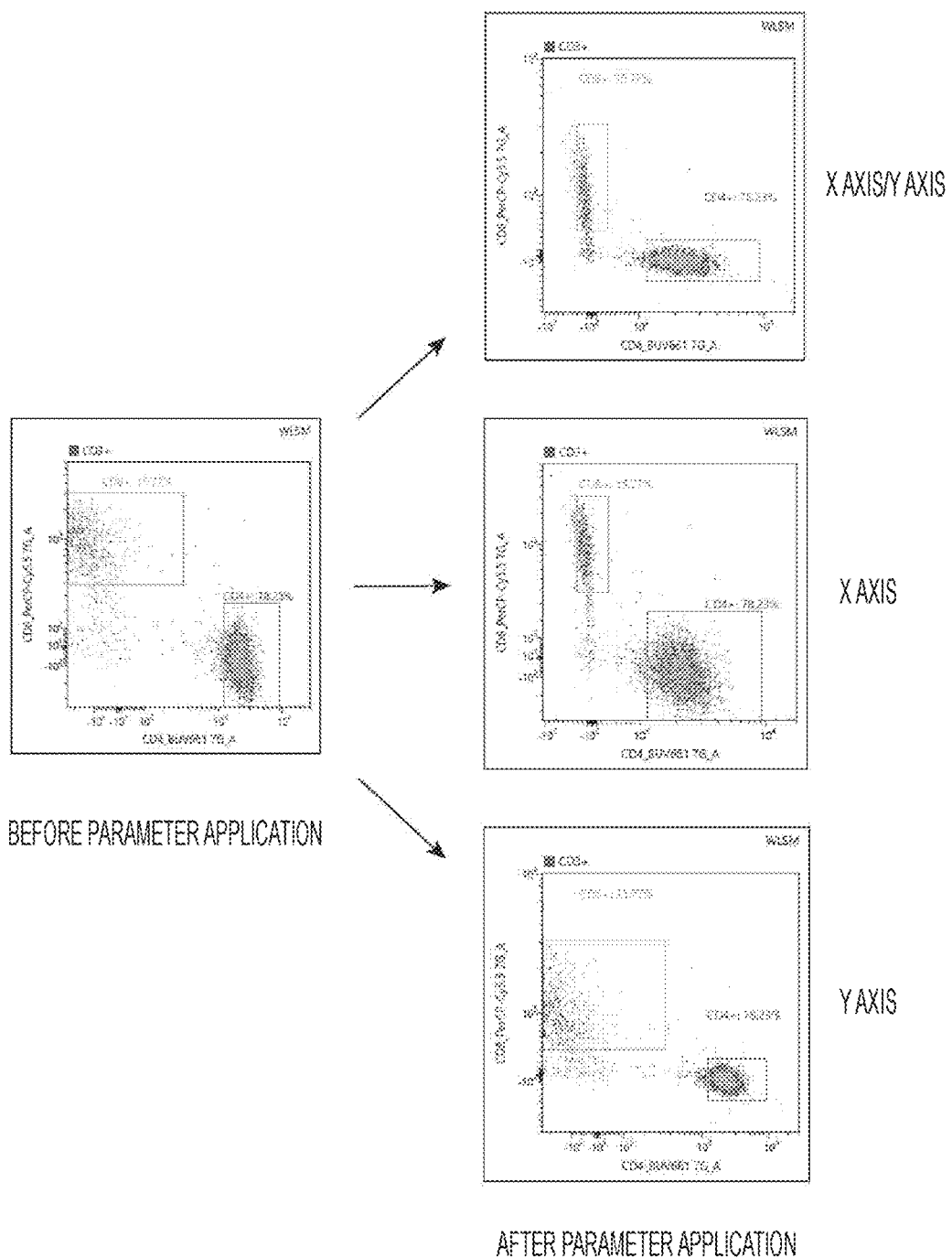
FIG. 6 is drawing-substituting graphs illustrating examples of graphs where the parameters are calculated for an X axis and a Y axis, only the X axis, and only the Y axis, and plot display is updated.

The information processing unit 11 can calculate the parameters on the basis of an instruction of a user. For example, as a trigger for calculating the various parameters, it is also possible to prepare various icons on the display unit 13 described later, calculate the corresponding parameters when the user clicks the corresponding icon, and update plot display. More specifically, for example, three icons of an X axis and a Y axis, only the X axis, and only the Y axis are prepared on the display unit 13 described later, the corresponding parameter is calculated in accordance with the clicked icon, and the plot display can be updated. FIG. 6 shows examples in which the parameter is calculated for each of the X axis and the Y axis, only the X axis, and only the Y axis, and the plot display is updated.

Figure 7:
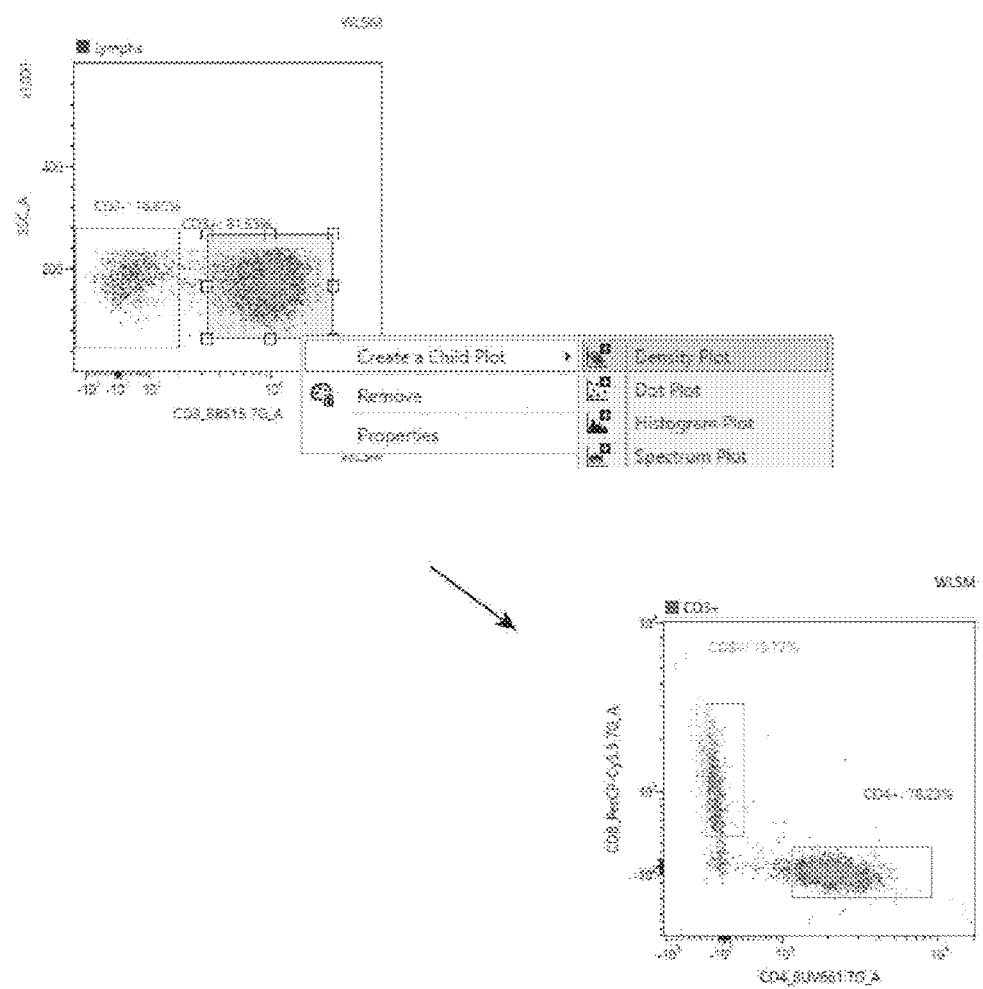
FIG. 7 is drawing-substituting graphs illustrating an example where a plot (child plot) is newly generated only for particle data existing in a gate.

After the graph illustrating the optical data is created on the display range optimized in this manner, as shown in FIG. 7, the user can also set a gate, newly generate a plot (child plot) for only the particle data existing in the gate, and repeat this process. When a child plot is generated, similarly to the above, the information processing unit 11 calculates various parameters, so that it is possible to obtain display of a child plot suitable for analysis.

In general, while in the case of a particle dispensing apparatus such as a cell sorter, there is a restriction on a possible parameter set due to memory restriction or the like, the restriction on the parameter set can be applied to the particle dispensing apparatus 3 such as a cell sorter by incorporating the restriction on the parameter set into an information processing technique of the present technology.

Furthermore, the information processing technique of the present technology can also be performed as pre-processing of particle analysis using a clustering technique. In recent years, in the field of particle analysis technology, since a number of colors and an amount of data to be analyzed have increased, time required for various analyses has increased. As a solution to this problem, by using a so-called advanced analysis technique such as clustering, attempts to automate data analysis have been actively made. In a case where the analysis is automated by clustering, input values to clustering are generally coordinate values in plot display coordinates. When the plot display coordinate values are input, even if sensor values are the same, the input values to the clustering technique change depending on scaling setting of a target plot. Furthermore, there is a problem that automation of an entire analysis flow cannot be realized unless the automation of the parameter calculation is realized. Therefore, by performing the information processing technique of the present technology as pre-processing of the particle analysis using the clustering technique, it is possible to realize the automation of the parameter calculation and consistency of the parameter values.

By using the information processing technique of the present technology, the population of the particles can be appropriately visualized, and the user can easily perform the particle analysis. Furthermore, by appropriately displaying the entire population of the particles, measurement data can be correctly and appropriately analyzed. In general, in a case where the measurement data exists on the axis, it is assumed that if the user overlooks the data, doubt is caused in analysis/interpretation of data. However, by using the information processing technique of the present technology, a risk thereof can be largely reduced.

(4-2) Storage Unit 12

The information processing apparatus 1, the particle measuring apparatus 2, the particle measuring system 20, the particle dispensing apparatus 3, and the particle dispensing system 30 according to the present technology can each include the storage unit 12 that stores various data. The storage unit 12 can store all items related to the measurement and the analysis such as, for example, the optical data from the particles detected by the light detection unit 22, the record of the information processing by the information processing unit 11, and the information such as the graph obtained by the information processing unit 11.

Furthermore, as described above, in the present technology, since the storage unit 12 can be provided in a cloud environment, it is also possible for each user to share various types of information recorded on the storage unit 12 on the cloud via a network.

Note that, in the present technology, the storage unit 12 is not essential, and various data can be stored using an external storage apparatus or the like.

(4-3) Display Unit 13

The information processing apparatus 1, the particle measuring apparatus 2, the particle measuring system 20, the particle dispensing apparatus 3, and the particle dispensing system 30 according to the present technology can each include the display unit 13 that displays various data. The display unit 13 can display all items related to the measurement and the analysis such as, for example, the optical data from the particles detected by the light detection unit 22, the record of the information processing by the information processing unit 11, and the information such as the graph obtained by the information processing unit 11.

In the present technology, the display unit 13 is not essential, and an external display apparatus may be connected. As the display unit 13, for example, a display, a printer, or the like can be used.

(4-4) User Interface 14

The information processing apparatus 1, the particle measuring apparatus 2, the particle measuring system 20, the particle dispensing apparatus 3, and the particle dispensing system 30 according to the present technology can each further include the user interface 14 that is a section for the operation of the user. The user can access and control each of the units through the user interface 14.

In the present technology, the user interface 14 is not essential, and an external operation apparatus may be connected. As the user interface 14, for example, a mouse, a keyboard, and the like can be used.

(5) Dispensing Unit 31

The particle dispensing apparatus 3 and the particle dispensing system 30 according to the present technology can each include the dispensing unit 31. In the dispensing unit 31, the particles are dispensed on the basis of the optical data detected by the light detection unit 22. For example, the dispensing unit 31 can dispense the particles downstream of the flow path P on the basis of an analysis result of a size, a form, an internal structure, and the like of the particles analyzed from the optical data. Hereinafter, a dispensing method will be described according to each embodiment.

For example, in the particle dispensing apparatus 3 shown in FIG. 3, for example, droplets are generated from an ejection port of the main flow path P13 by applying vibration to the whole or a part of the main flow path P13 using a vibration element 31*a* or the like that vibrates at a predetermined frequency. Note that, in this case, the vibration element 31*a* to be used is not particularly limited, and a known vibration element can be freely selected and used. A piezoelectric vibration element and the like can be exemplified. Furthermore, by adjusting amounts of liquid fed to the sample liquid flow path P11, the sheath liquid flow paths P12*a*, P12*b*, and the main flow path P13, a diameter of the ejection port, the frequency of the vibration element, and the like, a size of each of the droplets can be adjusted, and the droplets each containing a certain amount of particles can be generated.

Next, positive or negative charges are charged on the basis of the analysis result of the size, the form, the internal structure, and the like of each of the particles analyzed on the basis of the optical information detected by the light detection unit 22 (see reference sign 31*b* in FIG. 3). Then, a path of each of the charged droplets is changed in a desired direction by counter electrodes 31*c* to which a voltage is applied, and the charged droplets are dispensed.

Furthermore, for example, in the embodiment shown in FIG. 4, three branch flow paths of a dispensing flow path P14 and disposal flow paths P15*a*, P15*b* are provided downstream of the main flow path P13 formed in the substrate T, and dispensing target particles that are determined to satisfy predetermined optical characteristics and are taken into a dispensing flow path P14, and non-dispensing target particles that are determined not to satisfy the predetermined optical characteristics are made to flow to any one of the two disposal flow paths P15*a*, P15*b* without being taken into the dispensing flow path P14, by which the dispensing can be performed.

The dispensing target particles can be taken into the dispensing flow path P14 using a known method, and for example, a negative pressure is generated inside the dispensing flow path P14 by the vibration element 31*a* such as a piezo element, and the sample liquid and the sheath liquid containing the dispensing target particles are sucked into the dispensing flow path P14 using the negative pressure. Furthermore, although not illustrated, by controlling or changing the laminar flow direction using a valve electromagnetic force, a fluid stream (gas or liquid), or the like, it is also possible to take the dispensing target particles into the dispensing flow path P14.

In the embodiment shown in FIG. 4, the completely closed type dispensing apparatus can be obtained by connecting a sample liquid storage unit B1 to the sample liquid flow path P11, a sheath liquid storage unit B2 to the sheath liquid flow paths P12*a*, P12*b*, a dispensed-liquid storage unit B3 to the dispensing flow path P14, and waste liquid storage units B4*a*, B4*b* to the disposal flow paths P15*a*, P15*b* in communication with each other. For example, in a case where the dispensing target particles are cells or the like for use in cell preparations or the like, in order to maintain a sterile environment and prevent contamination, it is preferable to design so as to be a completely closed type (isolated from an external environment) as in the embodiment shown in FIG. 4.

<2. Information Processing Method, Particle Measuring Method, and Particle Dispensing Method>

An information processing method according to the present technology is a method for receiving the optical data obtained from the particles and processing the received optical data, and at least performs an information processing step. Furthermore, a storage step, a display step, and the like can be performed as necessary. The particle measuring method according to the present technology performs at least a light detection step and the information processing step. Furthermore, a light irradiation step, the storage step, the display step, and the like can be performed as necessary. The particle dispensing method according to the present technology performs at least the light detection step, the information processing step, and a dispensing step. Furthermore, the light irradiation step, the storage step, the display step, and the like can be performed as necessary. Note that details of each of the steps are the same as the steps performed by each of the units of the information processing apparatus 1, the particle measuring apparatus 2, the particle measuring system 20, the particle dispensing apparatus 3, and the particle dispensing system 30 according to the present technology described above, and thus description thereof is herein omitted.

<3. Information Processing Program>

An information processing program according to the present technology is a program used to receive the optical data obtained from the particles, and process the received optical data, the program causing a computer to implement an information processing function of calculating the parameter that specifies the display range of the optical data having at least one axis including the linear axis and the logarithmic axis on the basis of the received optical data, in which the parameters includes the first parameter that specifies the range of the linear axis and the second parameter that specifies the lower limit value of the display range, and the first parameter and the second parameter are calculated on the basis of different reference values.

The information processing program according to the present technology is recorded on an appropriate recording medium. Furthermore, the information processing program according to the present technology can also be used by being stored in a cloud environment or the like and being downloaded by the user to a personal computer or the like via a network. Note that the information processing function in the information processing program according to the present technology is the same as the information processing function performed by of the information processing unit 11 in each of the information processing apparatus 1, the particle measuring apparatus 2, the particle measuring system 20, the particle dispensing apparatus 3, and the particle dispensing system 30 described above, and thus description thereof is herein omitted.

Note that the present technology can also have the following configurations.

(1)

An information processing apparatus including an information processing unit that receives optical data obtained from particles, and
- calculates a parameter that specifies a display method of the optical data in a display range having at least one axis including a linear axis and a logarithmic axis on the basis of the received optical data,
- in which the parameter includes a first parameter that specifies a range of the linear axis and a second parameter that specifies a lower limit value of the display range, and
- the first parameter and the second parameter are calculated on the basis of different reference values.

(2)

The information processing apparatus according to (1),
- in which the display range has at least two axes including the linear axis and the logarithmic axis, and
- the information processing unit calculates the parameter for each of at least the two axes.

(3)

The information processing apparatus according to (1) or (2), in which the parameter further includes a third parameter that specifies an upper limit value of the display range.

(4)

The information processing apparatus according to any one of (1) to (3), in which the information processing unit calculates the first parameter by a following formula (1)

$$W = \mathrm{Log}(\mathrm{abs}(r)/(d))$$

$$(r = (n)\mathrm{percentile} \times (m)). \tag{1}$$

(5)

The information processing apparatus according to (4), in which the information processing unit calculates the second parameter by a following formula (2)

$$\mathrm{Min} = (c)\mathrm{percentile} \tag{2}$$

(6)

The information processing apparatus according to (5),
- in which the parameter further includes a third parameter that specifies an upper limit value of the display range, and
- the information processing apparatus calculates the third parameter by a following formula (3)

$$\mathrm{Max} = (a)\mathrm{percentile} \times (b) \tag{3}$$

(7)

The information processing apparatus according to (5) or (6),
- in which the parameter further includes a fourth parameter that specifies a range of the linear axis of data of a negative area in the optical data, and
- the information processing unit calculates the fourth parameter by a following formula (4)

$$A = \mathrm{Log}(\mathrm{Min}/r)$$

$$(r = (n)\mathrm{percentile} \times (m)). \tag{4}$$

(8)

The information processing apparatus according to any one of (1) to (7), in which the information processing unit calculates the parameter on the basis of an instruction of a user.

(9)

The information processing apparatus according to (8), further including a storage unit that stores the optical data,
- in which the information processing unit calculates the parameter on the basis of optical data received from the storage unit on the basis of an instruction of the user.

(10)

The information processing apparatus according to any one of (1) to (9), in which the information processing unit creates a graph illustrating the optical data on the display range using the display method specified on the basis of the parameter.

(11)

The information processing apparatus according to (10), further including a storage unit that stores the graph.

(12)

A particle measuring apparatus including:
- a light detection unit that detects optical data from particles flowing in a flow path; and
- an information processing unit that receives the detected optical data, and
- calculates a parameter that specifies a display method of the optical data in a display range having at least one axis including a linear axis and a logarithmic axis on the basis of the received optical data,
- in which the parameter includes a first parameter that specifies a range of the linear axis and a second parameter that specifies a lower limit value of the display range, and
- the first parameter and the second parameter are calculated on the basis of different reference values.

(13)

A particle measuring system including:
- a light detecting apparatus that detects optical data from particles flowing in a flow path; and
- an information processing apparatus having an information processing unit that receives the detected optical data, and
- calculates a parameter that specifies a display method of the optical data in a display range having at least one axis including a linear axis and a logarithmic axis on the basis of the received optical data,
- in which the parameter includes a first parameter that specifies a range of the linear axis and a second parameter that specifies a lower limit value of the display range, and
- the first parameter and the second parameter are calculated on the basis of different reference values.

(14)

A particle dispensing apparatus including:
- a light detection unit that detects optical data from particles flowing in a flow path;
- an information processing unit that receives the detected optical data, and
- calculates a parameter that specifies a display method of the optical data in a display range having at least one axis including a linear axis and a logarithmic axis on the basis of the received optical data,
- in which the parameter includes a first parameter that specifies a range of the linear axis and a second parameter that specifies a lower limit value of the display range, and the first parameter and the second parameter are calculated on the basis of different reference values; and
a dispensing unit that dispenses the particles on the basis of the detected optical data.

(15)
A particle dispensing system including:
a light detecting apparatus that detects optical data from particles flowing in a flow path;
an information processing apparatus having an information processing unit that receives the detected optical data, and
calculates a parameter that specifies a display method of the optical data in a display range having at least one axis including a linear axis and a logarithmic axis on the basis of the received optical data,
in which the parameter includes a first parameter that specifies a range of the linear axis and a second parameter that specifies a lower limit value of the display range, and
the first parameter and the second parameter are calculated on the basis of different reference values; and
a dispensing apparatus that dispenses the particles on the basis of the detected optical data.

(16)
An information processing method including an information processing step of receiving optical data obtained from particles, and
calculating a parameter that specifies a display method of the optical data in a display range having at least one axis including a linear axis and a logarithmic axis on the basis of the received optical data,
in which the parameter includes a first parameter that specifies a range of the linear axis and a second parameter that specifies a lower limit value of the display range, and
the first parameter and the second parameter are calculated on the basis of different reference values.

(17)
An information processing program that causes a computer to implement an information processing function of receiving optical data obtained from particles,
calculating a parameter that specifies a display method of the optical data in a display range having at least one axis including a linear axis and a logarithmic axis on the basis of the received optical data,
in which the parameter includes a first parameter that specifies a range of the linear axis and a second parameter that specifies a lower limit value of the display range, and
the first parameter and the second parameter are calculated on the basis of different reference values.

REFERENCE SIGNS LIST

1 Information processing apparatus
2 Particle measuring apparatus
20 Particle measuring system
3 Particle dispensing apparatus
30 Particle dispensing system
P Flow path
21 Light irradiation unit
22 Light detection unit
11 Information processing unit
12 Storage unit
13 Display unit
14 User interface
31 Dispensing unit

The invention claimed is:

1. An information processing apparatus comprising:
a computer configured to:
receive optical data obtained from particles;
calculate a parameter that specifies a method of displaying the optical data in a display range, wherein a display of the optical data has at least one axis including a linear axis and a logarithmic axis on a basis of the received optical data,
wherein the parameter includes a first parameter that specifies a range of the linear axis and a second parameter that specifies a lower limit value of the display range, and
the first parameter and the second parameter are calculated on a basis of different reference values; and
control display of the optical data on a display device based on the first parameter and the second parameter.

2. The information processing apparatus according to claim 1,
wherein the display has at least two axes including the linear axis and the logarithmic axis, and
the computer is configured to calculate the parameter for each of at least the two axes.

3. The information processing apparatus according to claim 1, wherein the parameter further includes a third parameter that specifies an upper limit value of the display range.

4. The information processing apparatus according to claim 1, wherein the computer is configured to calculate the first parameter by a following formula (1)

$$W = \mathrm{Log}(\mathrm{abs}(r)/(d))$$

$$(r=(n)\mathrm{percentile} \times (m)). \quad (1)$$

5. The information processing apparatus according to claim 4, wherein the computer is configured to calculate the second parameter by a following formula (2)

$$\mathrm{Min} = (c)\mathrm{percentile} \quad (2).$$

6. The information processing apparatus according to claim 5,
wherein the parameter further includes a third parameter that specifies an upper limit value of the display range, and
the computer is configured to calculate the third parameter by a following formula (3)

$$\mathrm{Max} = (a)\mathrm{percentile} \times (b) \quad (3).$$

7. The information processing apparatus according to claim 5,
wherein the parameter further includes a fourth parameter that specifies a range of the linear axis of data of a negative area in the optical data, and
the computer is configured to calculate the fourth parameter by a following formula (4)

$$A = \mathrm{Log}(\mathrm{Min}/r)$$

$$(r=(n)\mathrm{percentile} \times (m)). \quad (4)$$

8. The information processing apparatus according to claim 1, wherein the computer is configured to calculate the parameter on a basis of an instruction of a user.

9. The information processing apparatus according to claim 8, further comprising a storage device that stores the optical data,
wherein the computer is configured to calculate the parameter on a basis of optical data received from the storage device on a basis of an instruction of the user.

10. The information processing apparatus according to claim 1, wherein the computer is configured to create a graph illustrating the optical data on the display range using the method specified on a basis of the parameter.

11. The information processing apparatus according to claim 10, further comprising a storage device that stores the graph.

12. A particle measuring apparatus comprising:
a light detection device that detects optical data from particles flowing in a flow path; and
a computer configured to:
receive the detected optical data;
calculate a parameter that specifies a method of the displaying optical data in a display range, wherein a display of the optical data has at least one axis including a linear axis and a logarithmic axis on a basis of the received optical data,
wherein the parameter includes a first parameter that specifies a range of the linear axis and a second parameter that specifies a lower limit value of the display range, and
the first parameter and the second parameter are calculated on a basis of different reference values; and
control display of the optical data on a display device based on the first parameter and the second parameter.

13. A particle measuring system comprising:
a light detecting apparatus that detects optical data from particles flowing in a flow path; and
an information processing apparatus having a computer configured to:
receive the detected optical data;
calculate a parameter that specifies a method of displaying the optical data in a display range, wherein a display of the optical data has at least one axis including a linear axis and a logarithmic axis on a basis of the received optical data,
wherein the parameter includes a first parameter that specifies a range of the linear axis and a second parameter that specifies a lower limit value of the display range, and
the first parameter and the second parameter are calculated on a basis of different reference values; and
control display of the optical data on a display device based on the first parameter and the second parameter.

14. A particle dispensing apparatus comprising:
a light detection device that detects optical data from particles flowing in a flow path;
a computer configured to
receive the detected optical data, and
calculate a parameter that specifies a method of displaying the optical data in a display range, wherein a display of the optical data has at least one axis including a linear axis and a logarithmic axis on a basis of the received optical data,
wherein the parameter includes a first parameter that specifies a range of the linear axis and a second parameter that specifies a lower limit value of the display range, and
the first parameter and the second parameter are calculated on a basis of different reference values; and
a dispensing device configured to dispense the particles on a basis of the detected optical data.

15. A particle dispensing system comprising:
a light detecting device configured to detect optical data from particles flowing in a flow path;
an information processing apparatus having a computer configured to:
receive the detected optical data, and
calculate a parameter that specifies a method of displaying the optical data in a display range, wherein a display of the optical data has at least one axis including a linear axis and a logarithmic axis on a basis of the received optical data,
wherein the parameter includes a first parameter that specifies a range of the linear axis and a second parameter that specifies a lower limit value of the display range, and
the first parameter and the second parameter are calculated on a basis of different reference values; and
a dispensing device configured to dispense the particles on a basis of the detected optical data.

16. An information processing method executed by a computer, the method comprising:
receiving optical data obtained from particles;
calculating a parameter that specifies a method of displaying the optical data in a display range, wherein a display of the optical data has at least one axis including a linear axis and a logarithmic axis on a basis of the received optical data,
wherein the parameter includes a first parameter that specifies a range of the linear axis and a second parameter that specifies a lower limit value of the display range, and
the first parameter and the second parameter are calculated on a basis of different reference values; and
controlling display of the optical data on a display device based on the first parameter and the second parameter.

17. A non-transitory computer readable medium storing instructions that, when executed by a computer, perform an information processing method comprising:
receiving optical data obtained from particles;
calculating a parameter that specifies a method of displaying the optical data in a display range, wherein a display of the optical data has at least one axis including a linear axis and a logarithmic axis on a basis of the received optical data,
wherein the parameter includes a first parameter that specifies a range of the linear axis and a second parameter that specifies a lower limit value of the display range, and
the first parameter and the second parameter are calculated on a basis of different reference values; and
controlling display of the optical data on a display device based on the first parameter and the second parameter.

* * * * *